United States Patent [19]

St. George et al.

[11] Patent Number: 5,898,078

[45] Date of Patent: Apr. 27, 1999

[54] PREPARATION OF FERRIC AMINOPOLYCARBOXYLATE SOLUTIONS HAVING IMPROVED STABILITY

[75] Inventors: George M. St. George; Stephen B. Willis, both of Lake Jackson; David A. Wilson, Richwood, all of Tex.

[73] Assignee: The Dow Chemical Company, Midland, Mich., MI

[21] Appl. No.: 09/010,783

[22] Filed: Jan. 22, 1998

[51] Int. Cl.⁶ .................................................. C07F 15/02
[52] U.S. Cl. ............................................................ 556/148
[58] Field of Search ............................................. 556/148

[56] References Cited

U.S. PATENT DOCUMENTS

| | | | |
|---|---|---|---|
| 3,767,689 | 10/1973 | Donovan et al. | 260/439 R |
| 3,867,419 | 2/1975 | Iwano et al. | 260/439 R |
| 4,364,871 | 12/1982 | Svatek et al. | 260/439 R |
| 4,438,040 | 3/1984 | Svatek et al. | 260/439 R |
| 4,558,145 | 12/1985 | Smith et al. | 556/148 |
| 5,110,965 | 5/1992 | Thunberg et al. | 556/118 |
| 5,717,123 | 2/1998 | St. George et al. | 556/148 |
| 5,763,634 | 6/1998 | St. George et al. | 556/148 |

*Primary Examiner*—Porfirio Nazario-Gonzalez

[57] ABSTRACT

A process for preparing a ferric chelate of an aminopolycarboxylic acid wherein an iron-containing material is reacted with an aminopolycarboxylic acid chelant in the presence of a base, which comprises employing reactants such that the molar ratio of chelant to iron is from about 0.8 to about 0.99, is disclosed. In preferred embodiments the chelate is a ferric ammonium ethylenediaminetetraacetic acid chelate. The inventive chelates show a reduced tendency to form a dark precipitate upon standing. This process is particularly suitable for use in preparing chelates for use in applications such as photographic bleaching. The corresponding ferric chelate composition and products prepared by the described process are also disclosed.

19 Claims, No Drawings

PREPARATION OF FERRIC AMINOPOLYCARBOXYLATE SOLUTIONS HAVING IMPROVED STABILITY

BACKGROUND OF THE INVENTION

In the photographic industry, the oxidation of metallic silver in photographic images or negatives to silver ion is known as bleaching. A desirable bleaching agent will react rapidly with silver and then react rapidly with air to regenerate the bleaching agent. Ferric compounds have been used for this purpose for decades. The ferric compound in the most widespread use today is ferric ammonium ethylenediaminetetraacetate because of its desirable redox properties and ease of preparation from inexpensive commercial chemicals (ferrosoferric oxide; ethylenediaminetetraacetic acid (EDTA); and ammonia).

As described by Donovan and Surash (U.S. Pat. No. 3,767,698, published Oct. 23, 1973) and by Svatek, et al. (U.S. Pat. No. 4,364,871, published Dec. 21, 1982, and U.S. Pat. No. 4,438,040, published Mar. 20, 1984), a ferric ammonium EDTA solution can be prepared by reacting iron oxide with a stoichiometric excess of ammoniated EDTA in an aqueous mixture at temperatures below 100° C. for less than three hours, followed by pH adjustment, aeration, and filtration. A more recent variation of the method, described by Thunberg, et al. (U.S. Pat. No. 5,110,965, published May 5, 1992), describes the use of ferrous salts to catalyze the reaction between the iron oxide and ammoniated EDTA.

Whereas chelate solutions made by the aforementioned process are useful for photographic bleaching, over time they show a tendency to precipitate fine, black, particulate matter which might be detrimental to the quality of photographs prepared using said solutions and which, in any case, may reduce customer acceptability of the product. It would be desirable, therefore, to produce ferric EDTA solutions, as well as other ferric-aminopolycarboxylic acid chelates, which are more stable against the formation of such dark particulates.

SUMMARY OF THE INVENTION

The present process reduces or eliminates formation or precipitation of these dark particulates (complete identification of composition presently unknown) through a simple adjustment of stoichiometry of the chelant to the iron. While in processes of the prior art the selected stoichiometry of chelant to iron was preferably a slight excess of chelant, such being employed to maximize the dissolution of the iron and thereby reduce the amount of insoluble iron remaining at the end of the reaction process, the present invention comprises selection of chelant:iron stoichiometry which is, surprisingly and effectively, reversed such that there is a slight excess of iron. This reversal can result in reduction or avoidance of the formation of dark particulates with time and/or temperature, producing a more visually acceptable product and also, in the case of ferric ammonium EDTA solutions in particular, possibly a more efficacious product for use in the photographic industry. Also described herein are a ferric chelate composition comprising iron and chelant in a molar ratio of chelant to iron of less than 1.0, and a ferric chelate product prepared by a process comprising reacting an iron-containing material with an aminopolycarboxylic acid chelant in the presence of a base, wherein the molar ratio of chelant to iron is from about 0.8 to about 0.99.

DESCRIPTION OF THE PREFERRED EMBODIMENTS

The present invention offers the advantage of being practicable with a variety of methods to prepare solutions of ferric-aminopolycarboxylic acid chelate from an iron source, a chelant, and a base. In particular, the present invention offers a method of preparing a solution of ferric ammonium EDTA from, preferably, ferrosoferric oxide, EDTA, and ammonia. While a variety of preparation conditions are contemplated, there do exist preferred embodiments which have been found to be particularly advantageous.

The general reaction scheme comprehends the production of a ferric chelate of an aminopolycarboxylic acid wherein an iron-containing material is reacted with an aminopolycarboxylic acid chelant in the presence of a base. This base is most conveniently and economically selected to be ammonia, in either aqueous or anhydrous form. Other bases, such as sodium hydroxide, potassium hydroxide, or mixtures of these with each other or with ammonia, can also be used. For purposes of this patent application, it will be understood that "ammonia" and "ammoniation" will be used generally to represent any base or contact therewith. In general, and as described in the prior art, the ammonia and chelant are preferably contacted in water, and simultaneously or thereafter contacted with a selected iron-containing material. This reactant mixture is then heated to produce a chelate, which is then preferably cooled and thereafter ammoniated to dissolve the iron chelate. This is followed by cooling again and oxidizing any ferrous iron to ferric iron.

The conditions under which this reaction is carried out play a significant role in the efficacy and economy with which the ferric animonium chelate can be produced. As noted hereinabove, the present invention requires control of one particular ratio, i.e. the chelant:iron molar ratio. Where the prior art employed excess chelant, the present invention employs a slight excess of iron, and thus the chelant:iron ratio is on the order of from about 0.8, preferably from about 0.9, more preferably from about 0.92, and most preferably from about 0.95, to about 0.99. Employment of materials within the preferred molar ratio ranges reduces the formation of the dark particulates and is preferably balanced against the need to reduce or minimize the amount of undissolved iron oxide remaining at the end of the process which must then be removed by filtration, which encourages the routine practitioner to select a ratio within one of the preferred ranges.

Control of the molar ratio of ammonia:chelant is also advantageously employed in carrying out the reaction of the present invention. Preferably the selected ratio of from about 0.5, more preferably from about 1.0, to about 1.8, more preferably to about 1.5, and most preferably to about 1.3. The amount of water used is selected so that the concentration of iron in the final chelate solution is generally from about 4 to 8 percent of iron by weight. Those skilled in the art will understand that this final solution represents a product particularly suitable for shipping, and that a consumer using it for purposes such as photobleaching may then dilute it further as desired.

The chelant can be selected from a variety of suitable aminopolycarboxylic acids, including but not limited to ethylenediaminetetraacetic acid ("EDTA"), 1,3-propanediaminetetraacetic acid ("PDTA"), nitrilotriacetic acid ("NTA"), ethylenediaminedisuccinic acid ("EDDS"), N-hydroxyethylethylenediaminetriacetic acid, diethylenetriaminepentaacetic acid, iminodiacetic acid, N-substituted iminodiacetic acid, and combinations thereof. Preferred for reasons of availability, economy and performance are EDTA, PDTA, NTA, EDDS and combinations thereof.

The iron-containing material can be selected from, for example, elemental iron, steel, oxides of iron such as ferrosoferric oxide ($Fe_3O_4$), ferric oxide ($Fe_2O_3$), and combinations thereof and the like. Preferred are elemental iron and ferrosoferric oxide ($Fe_3O_4$), and more preferred is ferrosoferric oxide.

While it is possible to combine concurrently the selected chelant, base and iron-containing material without regard to order of mixing, preferred mixing order is first to treat or contact the chelant with the base such as ammonia to form a resultant product, and then to treat or contact the resultant product with the iron-containing material. This order of procedure enables convenient handling of materials due to rheology factors involved in processing.

Once the three-part reaction mixture is formed, it is then necessary to heat it to a temperature sufficiently high to initiate chelation of the iron. Chelation typically is accomplished at a temperature from about 65° C., preferably from about 80° C., more preferably from about 90° C., to about 110° C., preferably to about 100° C. The reaction mixture is preferably held at a given temperature for a time sufficient to dissolve the iron, which in the more preferred temperature range of from about 90° C. to about 100° C., is preferably from about one minute, more preferably from about five minutes, to about sixty minutes, more preferably to about thirty minutes. Lower temperatures may result in reaction times which are efficacious but commercially unacceptable, while higher temperatures may undesirably degrade the chelant.

Following the heating/chelation step, it is advantageous to cool the chelate solution prior to pH adjustment. This helps to offset the effect of the exotherm which results from addition of a base, and particularly ammonia, which can increase chelant degradation or create process problems such as flashing of the ammonia. This cooling is preferably to a temperature from about 25° C., more preferably from about 30° C., most preferably from about 40° C., to about 65° C., more preferably to about 60° C., and consideration is desirably given to balance cooling needs against cooling costs. Ammonia (or other base) is then added to bring the solution to a desirable pH, generally between 7 and 8 for applications such as photobleaching in which pH control increases solution stability, while keeping the temperature below 70° C.

It is also desirable to treat the solution to oxidize any ferrous iron remaining to the ferric form, in order to optimize the oxidizing/bleaching capability of the chelate solution. Preferably this is accomplished via contacting with air or other oxygen-containing and otherwise inert material until the amount of ferrous iron remaining is essentially nil.

In a final step, it is known in the art that it is desirable to filter the product of the previous steps in order to remove insolubles such as undissolved iron. Conventional filtration methods and means may be advantageously employed. A relatively fine filter mesh grade is preferred, desirably from about 0.1 to about 10 microns, and for many applications a 0.5 micron mesh filter has been found to be efficacious. The final product is preferably one which exhibits significantly reduced tendency to form dark particulates upon exposure to time and/or temperature when compared with a product prepared under essentially identical conditions except that the molar ratio of chelant to iron, in the starting materials as well as in the final product, is 1.00 (unity) or greater. This reduced tendency can be measured visually, either over time or, where such is inconvenient, by employing an accelerated stability test. For clarification purposes it should be noted that there may be a difference between the chelant:iron molar ratios in the starting materials and the ratios in a composition of the present invention, which may be a product prepared by the process of the present invention; however, such molar ratio in either case would be less than 1.00 (unity), and in the case of the starting materials in particular is from about 0.8 to about 0.99.

One accelerated stability test which is useful in determining performance of the present invention is as follows: A product solution is prepared according to the teachings of the present invention and then charged to a high-density polyethylene bottle. This bottle is stored in a constant-temperature oven at 50° C. At appropriate intervals (every few days), a 125-ml sample of the solution is diluted with 125 ml of deionized water; and the resulting solution is passed through a 0.45-micron cellulose acetate filter (25-mm diameter). Failure (loss of solution stability) is recognized at the time where the diluted solution leaves a black residue which is visible on the filter.

The invention will be further clarified by a consideration of the following examples, which are intended to be exemplary of the present invention and should not be construed to limit its scope in any way.

EXAMPLE 1

A 2-liter beaker is charged with ethylenediaminetetraacetic acid (EDTA)(730 g, 2.50 moles); deionized water (690 g); 28 percent solution of aqueous ammonia (170 g, 2.80 moles); and $Fe_3O_4$ (200 g, 2.59 moles Fe). The molar ratio of chelant:iron is therefore 0.97. With vigorous stirring, the temperature is raised to 90° C. over the course of about 50 minutes and maintained there for about 30 minutes. The resulting solution is then allowed to cool to 60° C. over the course of about one hour. More of the 28 percent aqueous solution of ammonia (120 g, 1.97 moles) is then added, which produces an exotherm to about 68° C. The solution is then cooled to about 50° C., sparged with air for about three hours, then filtered through a 0.45-micron mesh nylon filter. 1765 g of product chelate solution is obtained and determined to contain 55.47 percent of [($NH_4$)FeEDTA•$NH_4OH$] by weight. This chelate solution is diluted with water to give a 47.41 percent solution and placed in a 50° C. oven for aging, using the stability test described in the specification hereinabove. Analytical data and results are given in the Table.

EXAMPLE 2

A 2-liter beaker is charged with EDTA acid (720 g, 2.46 moles); deionized water (690 g); 28% aqueous ammonia solution (165 g, 2.71 moles); and $Fe_3O_4$ (200 g, 2.59 moles Fe). The molar ratio of chelant:iron is therefore 0.95. With vigorous stirring, the mixture is heated to about 90° C. over the course of about 50 minutes and maintained there for about 30 minutes. The mixture is then cooled to about 60° C. over the course of about 60 minutes; and more of the 28 percent aqueous ammonia solution (115 g, 1.89 moles) is added, resulting in a temperature rise to 68° C. The solution is then cooled to about 50° C. and sparged with air for about 3.5 hours. After dilution with water and filtration through a 0.45-micron mesh nylon filter, 2017 g of product is obtained. Analytical data and results are given in the Table.

EXAMPLE 3 (COMPARATIVE)

A 2-liter beaker is charged with deionized water (600 g); $Fe_3O_4$ (171 g, 2.22 moles Fe); a 28 percent aqueous ammonia solution (67.5 g, 1.11 mole); and EDTA acid (700 g, 2.40 moles). With vigorous stirring, the thick slurry is heated to 65° C. over the course of about 15 minutes; and FeSO$_4$·7H$_2$O (6.1 g, 0.022 mole) is added. The molar ratio of chelant:iron is therefore 1.08. After a brief exotherm to 70° C., the temperature returns to 65° C. and is kept there for six hours. The solution is then cooled to 35° C. over the course of about 50 minutes. A 28 percent aqueous ammonia solution (204 g, 3.35 moles), pre-cooled to 0° C., is added, resulting in an exotherm to about 55° C. The solution is sparged with air overnight; and then additional 28 percent aqueous ammonia solution (21 g, 0.35 mole) is added. The resulting solution is filtered through a 0.45-micron nylon filter, giving 1738 g of product. Analytical data and results are given in the Table.

EXAMPLE 4 (COMPARATIVE)

A 2-liter beaker is charged with EDTA acid (770 g, 2.63 moles); deionized water (700 g); 28 percent aqueous ammonia solution (175 g, 2.88 moles); and Fe$_3$O$_4$ (200 g, 2.59 moles Fe). The molar ratio of chelant:iron is therefore 1.02. With vigorous stirring, the temperature is raised to 90° C. over the course of about 50 minutes and maintained there for another 30 minutes. The mixture is cooled to about 60° C. over the course of about 60 minutes; and more of the 28 percent aqueous ammonia solution (125 g, 2.06 moles) is added, causing a rise in temperature to about 69° C. The solution is cooled to 50° C., air-sparged for about 21 0 minutes, diluted with water, and then filtered through a 0.45-micron mesh nylon filter, giving 2006 g of product. Analytical data and results are given in the Table.

EXAMPLE 5

A two-liter beaker is charged with EDTA acid (870 g, 2.98 moles); deionized water (860 g); 28 percent aqueous ammonia solution (200 g, 3.28 moles); and Fe$_3$O$_4$ (250 g, 3.24 moles Fe). The molar ratio of chelant:iron is therefore 0.92. With vigorous stirring, the mixture is heated to about 90° C. over the course of about 50 minutes and maintained there for about 30 minutes. The mixture is cooled to about 63° C. over the course of about 50 minutes; and more of the 28 percent aqueous ammonia solution (115 g, 1.89 moles) is added, causing a temperature rise to about 72° C. The resulting mixture is then cooled to about 35° C. and filtered to remove unreacted Fe$_3$O$_4$ (6 g). Of the resulting 2254 g of solution, 510 g is separated for other studies, and the remainder is air-sparged at about 40° C. for about 3.0 hours. After dilution with water and filtration through a 0.45-micron mesh nylon filter, 1862 g of product is obtained. Analytical data and results are given in the Table.

TABLE

| Solution | EDTA:Fe* | Assay** | Days to Failure*** |
| --- | --- | --- | --- |
| Example 1 | 0.97 | 47.41 | 19 |
| Example 2 | 0.95 | 47.04 | >20 |
| Example 3 (Comp.) | 1.08 | 49.04 | 5 |
| Example 4 (Comp.) | 1.02 | 50.04 | 5 |
| Example 5 | 0.92 | 50.09 | >20 |

*molar ratio of initial charges
**weight percent of solution as (NH$_4$)FeEDTA.NH$_4$OH
***days at 50° C. until the stability test shows visible black precipitate

What is claimed is:

1. A process for preparing a ferric chelate of an aminopolycarboxylic acid wherein an iron-containing material is reacted with an aminopolycarboxylic acid chelant in the presence of a base, which comprises employing reactants such that the molar ratio of chelant to iron is from about 0.8 to about 0.99.

2. The process of claim 1 wherein the molar ratio of chelant to iron is from about 0.9 to about 0.99.

3. The process of claim 2 wherein the molar ratio of chelant to iron is from about 0.95 to about 0.99.

4. The process of claim 1 wherein the molar ratio of base to chelant is from about 0.5 to about 1.8.

5. The process of claim 1 wherein the aminopolycarboxylic acid is ethylenediaminetetraacetic acid, 1,3-propanediaminetetraacetic acid, nitrilotriacetic acid, ethylenediaminedisuccinic acid, N-hydroxyethylethylenediaminetriacetic acid, diethylenetriaminepentaacetic acid, iminodiacetic acid and its N-substituted derivatives, or a combination thereof.

6. The process of claim 5 wherein the aminopolycarboxylic acid is ethylenediaminetetraacetic acid, 1,3-propanediaminetetraacetic acid, ethylenediaminedisuccinic acid, nitrilotriacetic acid, or a combination thereof.

7. The process of claim 6 wherein the aminopolycarboxylic acid is ethylenediaminetetraacetic acid.

8. The process of claim 1 wherein the iron-containing material is an oxide of iron, elemental iron, steel, or a combination thereof.

9. The process of claim 8 wherein the oxide of iron is ferrosoferric oxide (Fe$_3$O$_4$).

10. The process of claim 1 wherein the base is aqueous ammonia, anhydrous ammonia, sodium hydroxide, potassium hydroxide, or a combination thereof.

11. A process for preparing a ferric ammonium chelate of an aminopolycarboxylic acid wherein an iron-containing material is reacted with an aminopolycarboxylic acid chelant in the presence of ammonia, which comprises the steps of (1) preparing an aqueous mixture of ammonia and aminopolycarboxylic acid chelant in a molar ratio of ammonia to chelant of from about 0.5 to about 1.8; (2) contacting therewith an iron-containing material in an amount such that the molar ratio of chelant to iron is from about 0.8 to about 0.99; (3) heating the product of step 2 sufficiently to produce a chelate; (4) cooling the product of step 3 sufficiently to avoid degradation of the chelate; (5) contacting the product of step 4 with ammonia in an amount sufficient to dissolve the product of step 4 and produce a stable solution; (6) contacting the product of step 5 with an oxygen source sufficient to oxidize ferrous iron to ferric iron; and (7) filtering the product of step 6.

12. The process of claim 11 wherein the aminopolycarboxylic acid is ethylenediaminetetraacetic acid, the iron-containing material is ferrosoferric oxide, the molar ratio of ethylenediaminetetraacetic acid to iron is from about 0.95 to about 0.99, the molar ratio of ammonia to chelant in step 1 is from about 1.0 to about 1.3, the mixture in step 3 is heated to a temperature greater than about 75° C., and the oxidation in step 6 is accomplished by contacting the chelate solution of step 5 with air.

13. The process of claim 12 wherein the temperature in step 3 is from about 90° C. to about 100° C.

14. A ferric chelate composition comprising iron and chelant in a molar ratio of chelant to iron of less than 1.0.

15. The composition of claim 14 wherein the molar ratio of chelant to iron is from about 0.95 to about 0.99.

16. The composition of claim 14 wherein the composition is a ferric ammonium chelate composition.

17. A ferric chelate product prepared by a process comprising reacting an iron-containing material with an aminopolycarboxylic acid chelant in the presence of a base, wherein the molar ratio of chelant to iron, in the starting materials, is from about 0.8 to about 0.99.

18. The ferric chelate product of claim 17 further comprising the steps of (1) preparing an aqueous mixture of ammonia and aminopolycarboxylic acid chelant in a molar ratio of ammonia to chelant of from about 0.5 to about 1.8; (2) contacting therewith an iron-containing material in an amount such that the molar ratio of chelant to iron is from about 0.9 to about 0.99; (3) heating the product of step 2 sufficiently to produce a chelate; (4) cooling the product of step 3 sufficiently to avoid degradation of the chelate; (5) contacting the product of step 4 with ammonia in an amount sufficient to dissolve the product of step 4 and produce a stable solution; (6) contacting the product of step 5 with an oxygen source sufficient to oxidize ferrous iron to ferric iron; and (7) filtering the product of step 6.

19. The ferric chelate product of claim 18 wherein the aminopolycarboxylic acid is ethylenediaminetetraacetic acid, the iron-containing material is ferrosoferric oxide, the molar ratio of ethylenediaminetetraacetic acid to iron is from about 0.95 to about 0.99, the molar ratio of ammonia to chelant in step 1 is from about 1.0 to about 1.3, the mixture in step 3 is heated to a temperature greater than about 75° C., and the oxidation in step 6 is accomplished by contacting the chelate solution of step 5 with air.

* * * * *